United States Patent [19]

Schattner

[11] 4,103,001

[45] Jul. 25, 1978

[54] BUFFERED PHENOL-GLUTARALDEHYDE STERILIZING COMPOSITIONS

[76] Inventor: Robert I. Schattner, 4000 Massachusetts Ave., NW., Washington, D.C. 20007

[21] Appl. No.: 718,579

[22] Filed: Aug. 30, 1976

[51] Int. Cl.² .................... A01N 11/00; A01N 9/00; A01N 9/24; A01N 9/26

[52] U.S. Cl. .................... 424/148; 424/333; 424/346

[58] Field of Search .................... 424/148, 333, 346

[56] References Cited

U.S. PATENT DOCUMENTS

| | | | |
|---|---|---|---|
| 3,057,775 | 10/1962 | Rendon | 424/333 |
| 3,282,775 | 11/1966 | Stonehill | 424/333 |
| 3,317,376 | 5/1967 | Schattner | 424/346 |
| 3,674,458 | 7/1972 | Schattner | 424/346 |
| 3,697,222 | 10/1972 | Sierra | 424/333 |
| 3,912,450 | 10/1975 | Boucher | 424/333 |
| 3,917,850 | 11/1975 | Boucher | 424/333 |
| 3,968,248 | 7/1976 | Boucher | 424/333 |
| 3,968,250 | 7/1976 | Boucher | 424/333 |

FOREIGN PATENT DOCUMENTS

| | | | |
|---|---|---|---|
| 1,432,324 | 4/1976 | United Kingdom | 424/333 |

OTHER PUBLICATIONS

McCutcheon's Detergents & Emulsifiers, 1971 Annual p. 154, Allured Publ. Corp., Ridgewood, N.J. (1971).

*Primary Examiner*—Albert T. Meyers
*Assistant Examiner*—D. W. Robinson
*Attorney, Agent, or Firm*—Fidelman, Wolffe & Waldron

[57] ABSTRACT

A room temperature aqueous sterilizing composition comprising from 0.75 –4.0% by wt. of glutaraldehyde and from 4–15% by wt of phenol and a metal phenate, preferably sodium phenate.

Optionally present are 1–5% by wt of sodium tetraborate, 2–10% by wt of a humectant such as glycerol, di-ethylene glycol or propylene glycol, and a surfactant. A preferred pH range is pH 7.0 – 7.4.

10 Claims, No Drawings

BUFFERED PHENOL-GLUTARALDEHYDE STERILIZING COMPOSITIONS

FIELD OF INVENTION

This invention relates to aqueous chemical compositions for room temperature sterilization with improved effectiveness and longer active life.

Efficient sterilization methods are needed for medical, hospital, and industrial applications. For repeated use, medical and dental instruments and equipment require sterilizing procedures which are safe, effective, and rapid. Yet, the existing procedures and methods are either cumbersome, time consuming, costly, or lack merit.

Chemical sterilization at room temperature has advantages over other means of sterilization and, consequently, has received considerable attention over the years. Many "cold sterilizing" compositions have been suggested to the art. For more detailed discussion of chemosterilizers and their modes of use, reference is made to "Chemical Sterilizers" by P. M. Borick in Advances in Applied Microbiology, Vol. 10, pages 291-312, (Academic Press, NY 1968).

In order to satisfy the criteria for sterilization, a chemical preparation must be capable of killing all forms of microbiological life, including spores which are highly resistant to sterilization. Such a chemical preparation must be bactericidal, fungicidal, and virucidal as well as sporicidal. While disinfectants, germicides, and antiseptics are capable of destroying most disease causing organisms, usually they are not cidal to (pathogenic) spores and, therefore, are not chemosterilizers. Relatively few antimicrobial agents are truly sporicidal and usable as chemosterilizers.

In recent years, the most widely used aqueous chemical sterilizing agent has been a buffered 2% glutaraldehyde solution. Glutaraldehyde solutions prepared with an acid pH are not ordinarily sporicidal at room temperature. However, when made alkaline, sporicidal activity in these solutions is very evident.

One of the problems encountered with alkaline glutaraldehyde solutions, however, is their lack of stability. Such solutions lose both their sporicidal activity and identifiable glutaraldehyde in about 2 weeks after they are made alkaline. Another problem with the alkaline 2% glutaraldehyde solution is the relatively long contact time (10 hours at room temperature) required for sterilization. Thus, the commercially available alkaline glutaraldehyde compositions exhibit limited active life and require lengthy immersion time for sterilization i.e., the suppliers advise against using the activated solution more than two weeks, and call for an immersion time of at least 10 hours at room temperature. Acid glutaraldehyde compositions are claimed to be relatively more stable than alkaline glutaraldehyde and have extended use life, but the acid glutaraldehyde compositions are not sporicidal at room temperature. For more detailed discussion of the glutaraldehyde sterilizer compositions heretofore suggested to the art, reference is made to U.S. Pat. Nos. 3,016,328, 3,282,775, and 3,697,222.

The composition of the present invention exhibits improvements in stability and active life, with the activated solution having a sterilizing use life of more than 30 days and sterilizing properties within 6¾ hours, at room temperature.

SUMMARY OF THE INVENTION

The present invention is an aqueous composition containing glutaraldehyde, 0.75-4.0% by weight, together with phenol and a metallic salt of phenol in total from 4-15%. The composition may also include, optionally, additional buffering agents, preferably 1-5% sodium tetraborate, anionic and/or nonionic surfactants in total from 2-10% and a humectant such as glycerol, propylene glycol or diethylene glycol from 2-10%.

RATIONALE OF THE INVENTION

Glutaraldehyde is acidic and, by itself, does not sterilize (i.e. is not sporicidal) at room temperatures. U.S. Pat. No. 3,016,328 teaches that by adding an appropriate alkaline buffer to glutaraldehyde, the resultant solution becomes an active sporicide in the pH range of 7.4 to 10.0. However, in alkaline solution, glutaraldehyde tends to polymerize and lose its sporicidal activity. Also, alkaline glutaraldehyde is not pH stable. Consequently, the alkaline glutaraldehyde sporicidal formulations tend to lose effectiveness over a period of time. As mentioned above, the various alkaline glutaraldehyde compositions marketed offer instructions not to use the (activated) solution after 14 days. A substantial increase in the active life of a buffered glutaraldehyde would constitute an advance in the art.

An additional area wherein improvement is desired is in kill time, this being the immersion period required for complete sterilization. Alkaline glutaraldehyde formulations with 2% glutaraldehyde as the only active ingredient are generally accepted to have a 10 hour sterilizing time. Increasing the glutaraldehyde concentration may help, but 4% glutaraldehyde is not significantly superior to 2% glutaraldehyde as a sporicide. Some improvement in kill time has been achieved by including formaldehyde as another active ingredient with glutaraldehyde. However, formaldehyde imparts unfavorable properties to the formulation because the composition then emits toxic vapors and a pungent odor.

Both alkaline and acid glutaraldehyde exhibit corrosive properties with respect to metals used in medical and dental instruments and apparatus. Presently marketed glutaraldehyde compositions contain rust inhibitors to prevent corrosion damage.

The compositions of this invention are a combination of buffered phenol and glutaraldehyde. Separately, phenol, phenolic derivatives or glutaraldehyde are not capable of room temperature sterilization. (Alkaline glutaraldehyde is, of course).

Buffered phenol compositions exhibit unusual properties (as witness the plant growth stimulation described in U.S. Pat. No. 3,674,458) which may not themselves cause lethality, but which might render microorganisms more susceptable to attack by the glutaraldehyde. Apparently, this is the rationale for improved sporicidal activity. Test studies indicate that the combination of buffered phenol and glutaraldehyde is substantially more effective than alkaline glutaraldehyde alone for room temperature sterilization.

Also, it has been found that the combination of glutaraldehyde and buffered phenol substantially increases the active life of, and imparts an inherent anti-corrosive property to, alkaline glutaraldehyde compositions. The buffered phenol/glutaraldehyde combination is effective at pH levels below 7.4 as well as in the more alkaline range above 7.4. However, a pH of below pH 7.4 is preferred because improvements in solution stability are apparent in this lower pH range.

DISCUSSION OF THE INVENTION

The buffered phenol/glutaraldehyde combination, particularly the preferred formulations, has an active sterilizing life of more than 30 days, requires 6¾ hours (and possibly less) immersion time to achieve complete sterilization at room temperature and does not require the addition of a special rust inhibitor. The buffered phenol composition, without glutaraldehyde therein, has a shelf-life of 5 years, or more.

The improvement in useful life and in kill time exhibited by the composition of the present invention is reflected by the improved stability. A more effective glutaraldehyde sterilizer composition will take longer to decline to the minimally acceptable effectiveness levels. An improvement in stability provides the user with a composition which retains a higher percentage of its original (kill) activity over the rated use period for the composition. Tests made on various proportions of buffered phenol and glutaraldehyde and on various phenol concentrations indicate that where stability improves effectiveness also improves.

Dilution studies, wherein the glutaraldehyde content is varied considerably, indicate that the sporicidal effectiveness of glutaraldehyde remains high in a glutaraldehyde concentration of 0.75-4.0% by weight. The dilution studies also indicate that the combination of buffered phenol and glutaraldehyde is far more bactericidal than either ingredient alone.

The fact that effectiveness has been improved by presence of buffered phenol also is evidenced by pH scan studies showing that the sporicidal activity of composition is less limited by pH. Specifically, the composition is effective over the range of pH 7-10 and apparently is effective at room temperature at pH less than pH-7. In practice, the pH range of 7.0-7.4 is preferred, because improved stability is believed to be achieved in this range. The composition may be adjusted to the desired pH by addition of hydrochloric acid or reduction of a buffer, or both.

The presence of sodium tetraborate (sodium borate) has been found to be useful as a buffering agent in quantities of from 1-5% by weight.

Also, a phenate, preferably sodium phenate 0.5-5% by weight, is a useful buffering agent. The concentration of phenol/phenate is a 4-15% with the phenol range being 3-10% by weight.

Surfactants are desirable ingredients, serving to facilitate penetration of active ingredients into pores, crevasses and irregular surfaces of objects being sterilized by immersion into the aqueous formulation.

In practice, presence of anionic and/or non-ionic surfactants individually or in various combinations, have been found effective. A combination of surfactants with a ratio of 60:40 to 40:60 anionic and non-ionic is preferred. Exemplary surfactants are sodium n-dodecylbenzene sulfonate and sodium cocoyl sarcosinate. The surfactants improve activity of the formulation. Tests with varying levels of surfactant concentration indicate that a high surfactant content, i.e., 2-10%, improve sporicidal activity for the composition as a whole.

Another ingredient that has been found desirable is a humectant selected from the group consisting of glycerol, propylene glycol and di-ethylene glycol, in quantities of from 2-10% by weight.

The full formulation can be provided in a two-container form, one container holding the glutaraldehyde, e.g. as 25% or 50% solution, and the other container holding the buffer system.

The specifically preferred embodiment of phenol/phenate buffer, which is detailed in Example A below at full strength, may be either diluted or made more concentrated within the range of about 0.4-1.5 times the full strength concentration given in Example A. Glutaraldehyde may be added to a final concentration of 0.75-4.0% by weight in the formulation. However, 2% glutaraldehyde is preferred.

For further understanding of this invention, the following specific examples of practice thereof are provided.

EXAMPLE A

The test formulation contained the following ingredients:

|   | I Buffered Phenol | % by wt. |
|---|---|---|
| a) | Phenol | 7.05 |
| b) | Sodium phenate | 1.20 |
| c) | Sodium borate | 2.35 |
| d) | Diethylene glycol | 6.30 |
| e) | Na-n-dodecyl benzene sulfonate (80% active material) | 7.00 |
| f) | Na cocoyl sarcosinate (30% active material) | 10.95 |
| g) | Distilled $H_2O$ | 50 + q.s. |
| h) | 6M hydrochloric acid | q.s. |
|   |   | 92.00 |
|   | II |   |
| 25% | Glutaraldehyde | 8.00 |
|   |   | 100.00 |

Procedure:

Add ingredients a-f to a tared container, then add a large portion of the distilled water and stir. (The solution may be heated to 45° C to facilitate solution). With stirring, add (6M) hydrochloric acid or sodium hydroxide until pH reaches whatever value is desired in the pH 7-10 range. The non-adjusted pH is about 9.5. Add sufficient additional distilled water to being to proper total mass. (If heating is not used to facilitate solution, addition of the hydrochloric acid will dissolve the solids as the pH nears 7.5).

The buffered phenol system and glutaraldehyde can be maintained in separate containers until needed. For use, the respective solutions are admixed.

EXAMPLE I

Procedures:

From culture of EPA designated strains of *Clostridium sporogenes* and *Bacillus subtilis* spores were grown, collected, coated on porcelain penicylinders and suture loops, and dried in partial vacuum exactly as described in the Official Final Action Sporicidal Test of the A.O.A.C. (*Official Methods of Analysis*, 11th Ed.).

To demonstrate adequate resistance of the spores, both types of carriers contaminated with both organisms (a total of four different combinations) were exposed to 2.5N HCl at 20° C exactly as described in the A.O.A.C. Sporicidal Test. The spores used in the testing procedures survived exposure to 2.5N HCl for 2-20 minutes.

A solution (pH 7.25) prepared according to Example A was tested for sporicidal activity with the carriers prepared as described above. The tests were run at 25°

C with 6¾ hours exposure using the procedures described in the Sporicidal Test of the A.O.A.C. To help neutralize any of the chemosterilizer which might be transferred with the carriers into the culture medium, a double tube transfer was made in fluid thioglycoate medium contained 0.5% "Tween80". The carriers in the culture medium were incubated, heat shocked, and reincubated as specified in the sporicidal testing procedure.

The sporicidal activity was tested on a total of 600 replicates as follows:

(a) Three samples representing three different preparations using both types of carriers (porcelain penicylinders and surgical silk suture loops) and both test organisms (*Bacillus subtilis* and *Clostridium sporogenes*). Thirty replicates were tested with each organism on each type of carrier, a total of 120 replicates or carriers for each sample.

(b) Duplicate samples of the formulation after a 60-day aging period using 30 replicates with both test organisms on both types of carriers. This was a total of 120 replicates or carriers for each sample.

Results

There were no positives in any of the 600 replicates.

EXAMPLE II

A. The formulation prepared as described in Example A was tested periodically over a five week period against *B. subtilis* spores to measure variation in "D" value at 25° C. over the five weeks (the D-value method employed herein being described in detail below). In addition the pH levels were measured. For control purposes a commercial alkaline glutaraldehyde sterilizer composition was similarly tested.

The results are tabulated below:

TABLE II

| Age of solution | Buffered Phenol/ Glutaraldehyde | | Commercial Alkaline Glutaraldehyde | |
|---|---|---|---|---|
| | D-value (25° C) | pH | D-value (25° C) | pH |
| Fresh | 14 min. | 7.30 | 32 min. | 8.15 |
| 1 week | 19 " | 7.28 | 44 " | 7.55 |
| 2 weeks | 14 " | 7.28 | 58 " | 7.45 |
| 3 weeks | — | 7.27 | — | 7.30 |
| 4 weeks | — | 7.22 | — | 7.30 |
| 5 weeks | 30 " | 7.12 | 140 " | 7.30 |
| Total change in pH over 5 week period | | 0.18 | | 0.85 |

The D-value method. To obtain the D-value of a given preparation, 0.1 ml of a *Bacillus subtilis* spore suspension, standaridized to contain $1 \times 10^8$ spores per ml, was pipetted into 10 ml of the test preparation which had been brought to thermoequilibrium in a 25° C water bath. This resulted in a concentration of $1 \times 10^6$ spores per ml of test preparation or agent. Immediately one ml of the test agent containing spores was withdrawn and transferred into a 99 ml sterile water blank containing 0.5% Tween-80. The blank was then shaken, diluted, and plated in Dextrose Agar (Difco) which also contained 0.5% Tween-80. After incubating the plates 48 hours at 37° C, the spores which survived grew into colonies which could be counted.

Plates were prepared in a similar manner from samples taken from the test agent at selected intervals from 5 to 45 minutes after the spores were added. The colonies, representing surviving spores, were counted for each time interval for a given test solution. These counts were converted into common logarithms and plotted against time. A line drawn through these points resulted in the characteristic death curve for the test solution used. From this plot, the time required to reduce the population of viable spores one log was calculated—thus the D-value was obtained for that test solution. Except where aging studies were conducted, the test agents were activated just prior to testing.

B. A 600-tube study as described in Example 1 was performed on a solution prepared according to Example A which had been activated (i.e. the buffer and glutaraldehyde was admixed) 30 days prior to testing. This study resulted in no positives in any of the 600 replicate tests at 6¾ hours contact.

EXAMPLE III

The composition of Example A was tested for corrosion and chemical reactivity against dental and hospital equipment commonly sterilized.

The formulation was inert to solid stainless steel and plated articles despite contact for up to 83 days at temperatures of from ambient to 45° C. Plated articles exhibited reactivity (by electrochemical corrosion) only where the plating had worn through to the carbon steel. A mild reactivity to aluminium was found.

The flexibility and elasticity of tubing and rubber articles were not impaired after 21 days exposure to the formulation at ambient temperatures. No softening or size variation could be detected in the moving or mating parts of a similarly exposed plastic syringe.

EXAMPLE IV

The buffered phenol composition of Example A was tested alone diluted 25% with distilled water (20 ml + 5 ml of $H_2O$) and in the diluted concentration with varying proportions of glutaraldehyde. (The quantity of $H_2O$ added was adjusted to compensate for the water content added with the 25% glutaraldehyde solution). The test organisms were *B. subtilis* spores. All test solutions were adjusted to pH 8.25. A commercially purchased alkaline glutaraldehyde sterilizer composition was used for control purposes.

The results are tabulated below:

TABLE IV

| Buffered Phenol | Glutaraldehyde Conc. | "D" value (25° C) |
|---|---|---|
| Full Strength | 0 | 15 hours |
| Diluted | 0 | 15 " |
| " | 0.25% | 225 minutes |
| " | 0.50% | 90 " |
| " | 0.75% | 39 " |
| " | 0.90% | 25 " |
| " | 1.00% | 13 " |
| " | 1.50% | 10 " |
| " | 2.00% | 8 " |
| Commercial alkaline Glutaraldehyde | 2.00% | 31 " |

EXAMPLE V

The formulation of Example A was prepared omitting the propylene glycol (humectant). A comparative test was conducted against the full formulation of Example A and a control (commercial alkaline glutaraldehyde sterilizer). *B. subtilis* spores were used at 25° C and at pH 8.25.

The tests showed that with or without propylene glycol the "D" values were less than 5 minutes. The commercial preparation "D" value was 45 minutes.

EXAMPLE VI

The consequence of relative dilution of the phenolic buffer and of glutaraldehyde are herein exemplified.

The phenolic buffer of Example A was diluted with distilled water as indicated in Table VI below. Glutaraldehyde was added in the wt. percent quantities indicated in Table VI below. All compositions were at pH 8.25 and were tested as freshly prepared solutions.

Tabulated below are D-25° C values for combinations of the phenolic buffer and glutaraldehyde.

TABLE VI

| Buffer Concentration | (D-values at 25° C) % Glutaraldehyde | | | | | |
|---|---|---|---|---|---|---|
| | 0.25 | 0.5 | 0.83 | 1.0 | 1.5 | 2.0 |
| 20% Buffer | 192 | 120 | 65 | 55 | 51 | 26 |
| 40% Buffer | 220 | 110 | 45 | 33 | 26 | 16 |
| 60% Buffer | 180 | 120 | 35 | 25 | 21 | 13 |
| 80% Buffer | 220 | 150 | 30 | 34 | 19 | 12 |
| Full Strength Buffer | 255 | 87 | — | 17 | — | 10 |

*D-value = Time in minutes to reduce the spore population by one log.

Also, 2% glutaraldehyde in full strength phenolic buffer, in 80% phenolic buffer and in 60% phenolic buffer, all freshly prepared, were tested at various pH levels from pH 7.0–8.3 against *B. subtilis* spores. "D" values 3–12 minutes were obtained, with the lower "D" values at the upper end of the pH range.

EXAMPLE VII

The effectiveness of the composition of Example A against gram positive and gram negative organisms is herein exemplified. The components (Table VII-B,C) and the full composition (Table VII-A) were tested at various concentrations. All dilutions were made with distilled water. The test used was the Use-Dilution test described in the AOAC 11th edition and the test organisms were those strains approved by the AOAC for this method.

The survival levels from each test are tabulated below:

TABLE VIIA

| Dilution of Phenolic Buffer + 2% Glutaraldehyde | Survival of Exposed Organisms | | |
|---|---|---|---|
| | Staphylococcus aureus ATCC 6538 | Salmonella choleraesuis ATCC 10708 | Pseudomonas aeruginosa ATCC 15442 |
| 1:2 | 0/10 | — | — |
| 1:4 | 0/10 | — | — |
| 1:8 | 0/10 | — | — |
| 1:10 | 0/10 | — | 0/20 |
| 1:16 | 0/10 | 0/10 | 0/40 |
| 1:20 | 0/10 | 0/10 | 0/50 |
| 1:30 | 0/10 | 0/10 | 0/10 |
| 1:40 | 0/10 | 0/10 | 3/20 |
| 1:50 | 0/30 | 0/20 | — |
| 1:60 | 0/10 | 2/20 | — |
| 1:64 | 0/10 | — | — |

TABLE VIIB

| Dilution of Phenolic Buffer (No glutaraldehyde) | Survival of Exposed Organisms | | |
|---|---|---|---|
| | Staphylococcus aureus | Salmonella choleraesuis | Pseudomonas aeruginosa |
| 1:4 | 1/10 | — | 0/10 |
| 1:8 | 0/10 | 0/10 | 1/10 |
| 1:10 | 5/10 | 0/10 2/10 | 5/10 |
| 1:20 | 10/10 | 9/10 | — |
| 1:30 | — | — | — |
| 1:40 | 10/10 | — | — |
| 1:50 | — | — | — |
| 1:60 | 10/10 | — | — |

TABLE VIIC

| Dilution 2% glutaraldehyde (No phenolic buffer) | Survival of Exposed Organisms | | |
|---|---|---|---|
| | Staphylococcus auerus | Salmonella choleraesuis | Pseudomonas aeruginosa |
| 1:2 | — | 0/10 | — |
| 1:4 | 0/10 | 0/10 | 0/10 0/10 |
| 1:8 | 0/10 | 0/10 | 0/10 0/10 |
| 1:10 | 1/10 | 2/10 | 0/10 10/10 |
| 1:20 | 10/10 | 5/10 | 0/10 10/10 |
| 1:30 | — | 10/10 | — |
| 1:40 | — | — | 10/10 |
| 1:50 | — | — | — |
| 1:60 | — | 10/10 | 10/10 |

TABLE VIID

Bactericidal effectiveness of the full formulation compared with each of the phenolic buffer and 2% glutaraldehyde as controls:

| Test Organism | Highest Dilution at Which Bactericidal | | |
|---|---|---|---|
| | Full Formulation | Buffer Alone | 2% Glut. Alone |
| Staphylococcus aureus | 1:64 | 1:8* | 1:8 |
| Salmonella cholerasuis | 1:50 | 1:8 | 1:8 |
| Pseudomonas aeruginosa | 1:30 | 1:4 | 1:8 |

*one test at 1:4 also had a positive

Conclusions

1. The results as summarized in Table VIID show a much greater bactericidal activity for the composition of Example A than for either component alone.

2. Of the three organisms tested, *Pseudomonas aeruginosa* is the most resistant to the disinfectant action of the complete formula. However, its resistance to the components separately did not differ materially from the resistance of the other two organisms.

What is claimed:

1. An aqueous sporicidal composition comprising by wt. from 0.75–4.0% glutaraldehyde and from 4–15% of a mixture of phenol and a metal phenate, the phenol content being from 3–10% and the metal phenate being from 0.5–5%, said composition further characterized in having a pH of about 7–10 and an active sterilizing life of at least 30 days.

2. The composition of claim 1 wherein from 1–5% by wt. of sodium tetraborate is present.

3. The composition of claim 1 wherein at least one anionic or non-ionic surfactant is present.

4. The composition of claim 3 wherein from 2–10% by wt. of surfactant is present.

5. The composition of claim 4 wherein the surfactant is selected from the group consisting of sodium dodecyl benzene sulfonate and sodium cocoyl sarcosinate.

6. The composition of claim 1 wherein from 2–10% by wt. of a humectant selected from the group consisting of glycerol, di-ethylene glycol and propylene glycol is present.

7. The composition of claim 1 wherein the phenol to sodium phenate ratio is 5–7 to 1.

8. An aqueous sporicidal composition comprising by weight the following ingredients:

| | % |
|---|---|
| phenol | 7.05 |
| sodium phenate | 1.20 |
| glutaraldehyde | 2.0 | said composition further characterized by having a pH of about 7–10 and an active sterilizing life of at least 30 days.

9. The composition of claim 8 wherein the composition further comprises by weight:

| | % |
|---|---|
| sodium tetraborate | 2.35 |
| diethylene glycol | 6.30 |
| sodium N-dodecyl benzene sulfonate | 5.6 |
| sodium cocoyl sarcosinate | 3.3 |

10. The composition of claim 9 wherein the pH is in the range of pH 7.0–7.4.

* * * * *